United States Patent [19]
Trebes et al.

[11] Patent Number: 6,134,300
[45] Date of Patent: Oct. 17, 2000

[54] MINIATURE X-RAY SOURCE

[75] Inventors: James E. Trebes, Livermore; Perry M. Bell, Tracy; Ronald B. Robinson, Modesto, all of Calif.

[73] Assignee: The Regents of the University of California, Oakland, Calif.

[21] Appl. No.: 09/186,555

[22] Filed: Nov. 5, 1998

[51] Int. Cl.⁷ .................................................. H01J 35/06
[52] U.S. Cl. ....................... 378/136; 378/121; 378/123; 378/137
[58] Field of Search ...................... 378/121, 123, 378/136, 137, 138

[56] References Cited

U.S. PATENT DOCUMENTS

| Re. 34,421 | 10/1993 | Parker et al. | 378/121 |
|---|---|---|---|
| 4,315,182 | 2/1982 | Furbee | 378/125 |
| 4,573,186 | 2/1986 | Reinhold | 378/138 |
| 4,689,809 | 8/1987 | Sohval | 378/136 |
| 4,764,947 | 8/1988 | Lesensky | 378/138 |
| 5,090,043 | 2/1992 | Parker et al. | 378/121 |
| 5,125,019 | 6/1992 | Evain et al. | 378/137 |
| 5,526,396 | 6/1996 | Jacob | 378/136 |
| 5,970,117 | 10/1999 | Basinger | 378/136 |
| 6,044,130 | 3/2000 | Inazura et al. | 378/138 |
| 6,064,718 | 5/2000 | Holland et al. | 378/122 |

*Primary Examiner*—David V. Bruce
*Assistant Examiner*—Allen C. Ho
*Attorney, Agent, or Firm*—Daryl S. Grzybicki; Alan H. Thompson; L. E. Carnahan

[57] ABSTRACT

A miniature x-ray source utilizing a hot filament cathode. The source has a millimeter scale size and is capable of producing broad spectrum x-ray emission over a wide range of x-ray energies. The miniature source consists of a compact vacuum tube assembly containing the hot filament cathode, an anode, a high voltage feedthru for delivering high voltage to the cathode, a getter for maintaining high vacuum, a connector for initial vacuum pump down and crimp-off, and a high voltage connection for attaching a compact high voltage cable to the high voltage feedthru. At least a portion of the vacuum tube wall is fabricated from highly x-ray transparent materials, such as sapphire, diamond, or boron nitride.

22 Claims, 2 Drawing Sheets

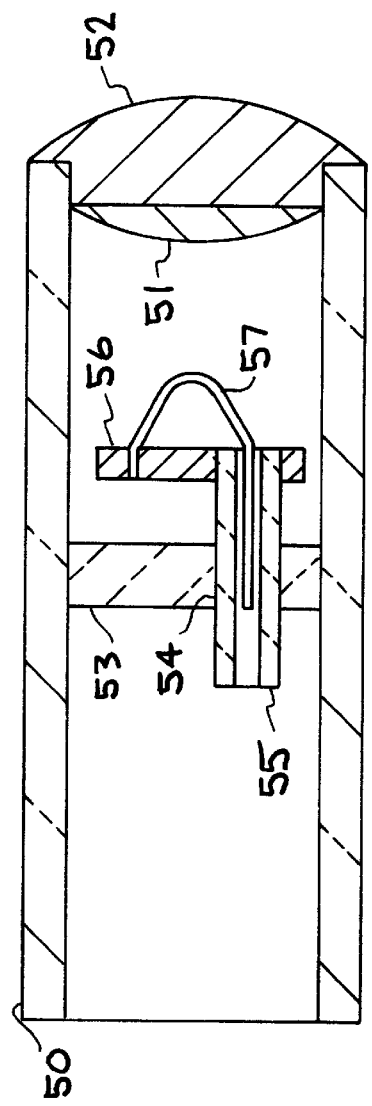
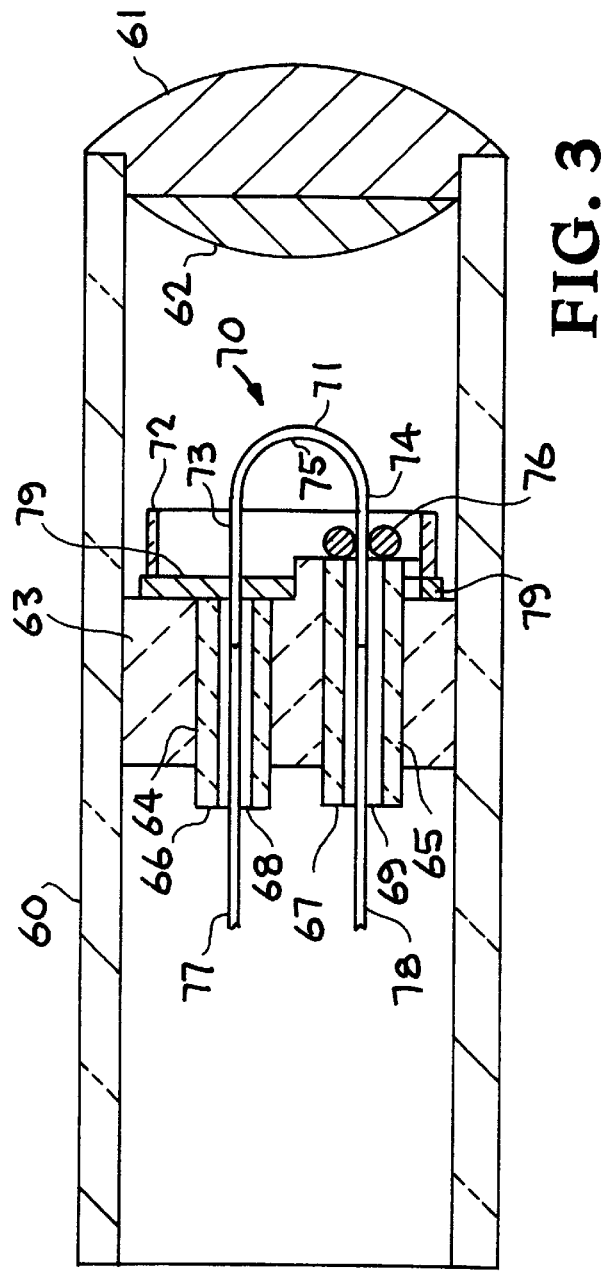

MINIATURE X-RAY SOURCE

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention is directed to x-ray sources, particularly to miniature x-ray sources, and more particularly to millimeter scale size x-ray sources using hot filament cathodes and which are capable of producing broad spectrum x-ray emission over a wide range of x-ray energies.

X-rays are typically produced in an assembly consisting of a vacuum housing, a high voltage feedthru, a high voltage connection to the feedthru, an anode, and a cathode. The system operates by applying high voltage across a gap between the anode and the cathode. Electrons are emitted by the cathode and accelerated by the high voltage to the anode. The electrons impact on the anode and create both broadband and line radiation through collisional excitation of the atoms within the anode. The x-rays are emitted from the anode and propagate through the vacuum housing to be used for any given application. The vacuum housing must be highly transparent to the x-rays or have a highly transparent window mounted in the vacuum housing to allow the x-rays to escape for use. The entire assembly is under vacuum to allow for efficient transport of the electrons from the cathode to the anode and prevent a gas discharge or an electrical arc from forming, which would significantly reduce the voltage across the gap (reducing the x-ray energy) or destroying the assembly. Efficient production of x-rays and the production with sufficient energy (5–40 keV or higher) for a wide range of applications requires the use of high voltages (5–40 kV or higher). The fabrication of compact x-ray sources has not been readily attainable until recently due to the need to have high voltage over extremely small dimensions (~1 mm), high vacuum in extremely small volumes (cubic mms), and a high voltage connection of extremely small size (~1 mm). Recently a miniature x-ray source which overcame the above-referenced limitation has been developed, and such is described and claimed in copending U.S. application Ser. No. 09/391,578, filed Sep. 8, 1999, entitled "Miniature X-Ray Source." In that miniature x-ray source, field emission type or cold cathodes were utilized.

The present invention constitutes an improvement over the miniature x-ray source of the above-referenced copending application by the use of hot filament cathodes. By way of example, a prototype hot filament cathode was tested with a 1–2 volt, 0.5–1.0 amps current used to heat a 25 micron diameter tungsten filament. The hot filament emits electrons which are then accelerated to the anode by the high voltage applied across the gap. Tests have shown that the miniature (millimeter scale size) x-ray source is capable of efficient production of x-rays with sufficient energy (~5–40 keV) for a wide range of applications which require the use of high voltages (~5–40 kV).

SUMMARY OF THE INVENTION

It is an object of the present invention to provide a miniature x-ray source.

A further object of the invention is to provide a hot filament cathode for a miniature x-ray source.

A further object of the invention is to provide a millimeter scale size x-ray source using a hot filament cathode.

Another object of the invention is to provide hot filament cathodes for millimeter scale size x-ray sources.

Another object of the invention is to provide a hot filament cathode of extremely small dimensions, which is capable of operation with high voltages (~5–40 kV).

Another object of the invention is to provide a millimeter scale size x-ray source using a hot filament cathode capable of efficient production of x-rays with sufficient energy (~5–40 keV) for a wide range of applications, including medical treatment and material analysis.

Other objects and advantages of the present invention will become apparent from the following description and accompanying drawings. As pointed out above, the present invention constitutes an improvement of the miniature x-ray source of the above-referenced copending application by the use of hot filament cathodes. Like the source of the above-referenced application, the millimeter scale size x-ray source of this invention is capable of producing broad spectrum x-ray emission over a wide range of x-ray energies and comprises a compact vacuum tube assembly containing the hot filament cathode, an anode, a high-voltage feedthru (but here delivering high voltage to the cathode rather than the anode), a getter for maintaining high vacuum, a connection for an initial vacuum pump down and crimp-off, and a high voltage connection for attaching a compact high voltage cable to the high voltage feedthru. The vacuum housing tube is preferably constructed of sapphire or diamond, but may be constructed of boron nitride or other highly x-ray transparent material.

The miniature x-ray source has numerous applications for medical treatment, such as arterial restenosis and cancer tumors, as well as for industrial applications, such as material analysis, wherein a compact x-ray source can be inserted into extremely confined spaces, such as inside the human body, or in close proximity to a material to be analyzed using x-ray analysis techniques.

BRIEF DESCRIPTION OF THE DRAWINGS

The accompany drawings, which are incorporated into and form a part of the disclosure, illustrate embodiments of the invention and, together with the description, serve to explain the principles of the invention.

FIG. 2 illustrates in cross-section another embodiment of a hot filament cathode for a miniature x-ray source.

FIG. 3 is a cross-sectional view of another embodiment of a millimeter scale size x-ray generator using a hot filament cathode.

DETAILED DESCRIPTION OF THE INVENTION

Figure 1:
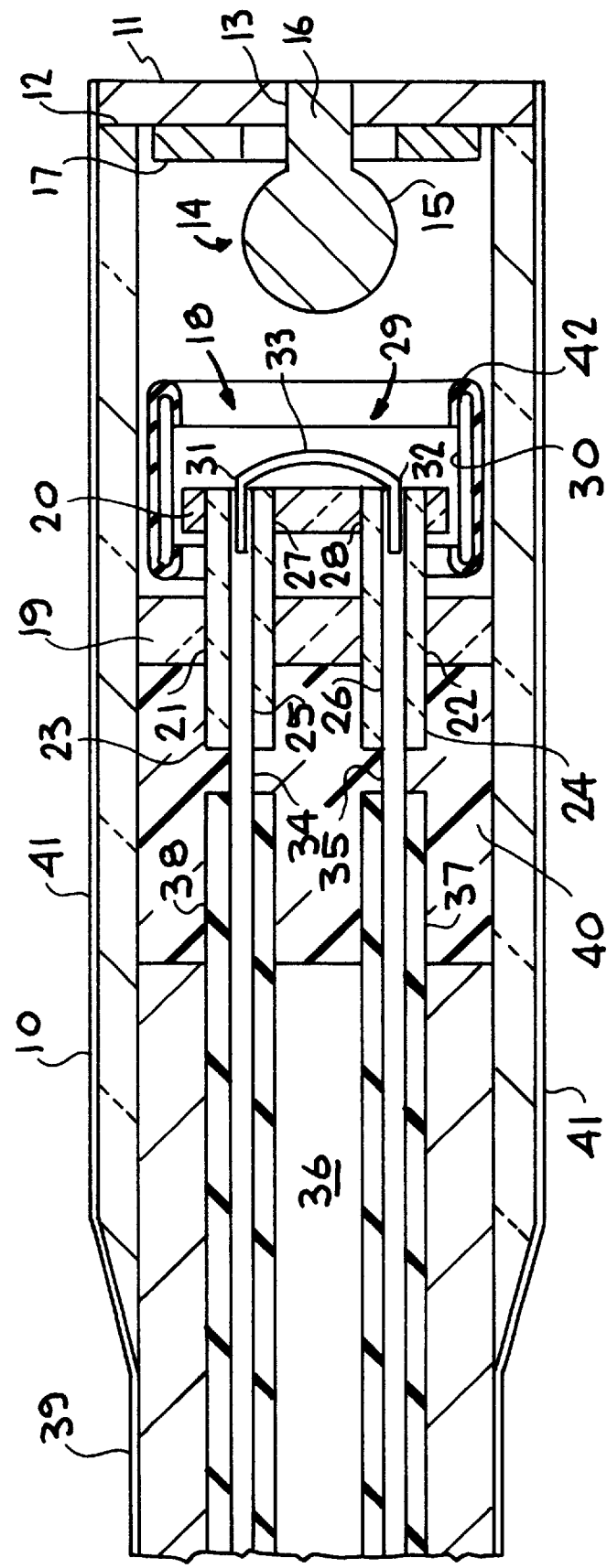
FIG. 1 is a cross-sectional view of a preferred embodiment of a miniature x-ray source with a hot filament cathode in accordance with the present invention.

The present invention is directed to a miniature x-ray source using a hot filament type cathode. The x-ray source has a millimeter scale size and is capable of producing broad spectrum x-ray emission over a wide range of energies. The invention is an improvement over the miniature x-ray source of above-referenced copending application Serial No. 09/391,578, and utilizes a hot filament type cathode in place of the cold or field emission type cathode, and thus the high voltage connections are to the cathode rather than the anode, as in the above-referenced copending application.

Advantages of Hot Filament Over Cold Cathode:

Independent control of electron current from the filament (cathode) to the anode.

Precise filament to anode gap not required.

Tolerance to surface conditions on the filament. Cold cathodes are extremely sensitive to surface conditions.

Tolerance to poor vacuum. Cold cathodes need $10^{-8}$ torr or better. Hot filament can operate at $10^{-5}$ torr or better.

Disadvantages:

Requires third wire.

Requires additional power to operate filament (hot cathode).

The miniature x-ray source of this invention finds use in the field of medical treatment requiring compact x-ray sources that can be placed in proximity to the region to be treated, such as arterial disease, cancer, restenosis, and tumors. The x-ray source also has industrial applications in material analysis, since the compact size has potential for remote operations which allows the source to be placed adjacent to the sample undergoing x-ray analysis, which improves the signal levels and allows for local measurements in confined or remote locations.

The miniature x-ray source consists of the following components: an anode, which, for example, may be composed of a tungsten ball on the end of a tungsten shaft, a hot filament type cathode spaced from the anode, at least one high voltage feedthru made, for example, of a ceramic material, a highly x-ray transparent vacuum housing made, for example, from sapphire, diamond, or pyrolytic boron nitride (PBN), a high voltage connection to a high voltage cable, a vacuum pump-out and crimp-off tube, and a getter. The anode is made from a high atomic number metal which produces x-rays with high efficiency under electron bombardment. Besides tungsten, the cathode may be made of tantalum, gold, or a gold coating over another conducting metal. The shape of the anode may be spherical, having, for example, a 1.3 mm diameter, or may be non-spherical, such as a cylindrical geometry with a rounded tip. The geometry of the anode needs to have rounded edges and smooth surfaces to minimize high electric fields and electrical arcing. For example, spherical anodes may be fabricated by heating a 0.5 mm diameter rod of material in an electrical arc and then rapidly removing the electrical power, whereby rapid cooling and surface tension produces a smooth sphere on the tip of the rod. The diameter of the sphere can be controlled by adjusting the electrical power or the heating duration.

The vacuum housing includes at least a section of highly x-ray transparent material, and may be composed of sapphire, diamond, PBN, alumina, glass, etc. The material of the vacuum housing—aside from being highly x-ray transparent—must be sufficiently strong to withstand the mechanical forces produced by both normal handling and the atmospheric forces pushing in on the evacuated assembly, and have a high electrical resistivity to minimize the potential for surface arcing and electrical breakdown.

When used, as in the above-referenced copending application, the vacuum pump-out and crimp-off tube may be made of various materials that can be crimped to produce a vacuum tight seal and be used for the vacuum pump down of the assembly, and may also serve as a location for placing a getter material to maintain the vacuum after crimp-off. The crimp-off may be made by a crimp-off tool, for example, that maintains tube diameter at the crimp joint, or by other means which result in a vacuum tight seal. The crimp is made once the vacuum in the assembly is sufficiently low for electrical operation (better than $10^{-6}$ torr), and once extended, bake-out has been achieved to minimize outgassing of the assembly components.

The bake-out process includes heating the tube to above 300° C. to drive out water vapor from the internal components. While under vacuum, the x-ray tube is operated with the electrical power to the filament and the bias voltage steadily increased until normal operating parameters are obtained. This allows electron emission from the filament, electron bombardment of the anode, and x-ray interactions with the internal surfaces to fully degas the internal components.

The crimp-off tube and process, as utilized in the above-referenced copending application, can be eliminated and the x-ray tube sealed with a vacuum brazing process after an extended bake-out at high vacuum. A metal end cap is utilized to close the vacuum housing, and could be used to hold the getter material in place, as shown in FIG. 1, described hereinafter. Alternatively, the getter can be manufactured in the shape of a donut and mounted at the base of the cathode, as shown in FIGS. 2 and 3, described hereinafter. This location is essentially electric field free and therefore the getter would present no internal electrical problems associated with surface arcing or breakdown.

The getter may, for example, be SAES ST 707, that activates after baking under vacuum at 300° C. for two hours. Any comparable getter could be used as long as the getter does not require any power or processing after activation.

The one or more high voltage feedthru consists, for example, of an alumina (ceramic) component with a cylindrical channel to allow the cathode filament end or ends to pass through to the exterior or to be connected to a high voltage cable. The one or more feedthrus can also be made of Maycor, or other electrically insulating materials. Since the feedthru, as seen in the drawings, extends to the exterior of the anode-cathode vacuum chamber (see FIG. 1), this minimizes the potential for arcing in the high voltage cable connection.

The high voltage connection, as shown in FIG. 1, for example, consists of a commercially available triaxial cable with two central conductors and a round shield, using Teflon or silicone insulation. The exterior insulation or ground shield and the insulation about each of the central conductors are stripped back, and the two conductors are soldered or otherwise secured to the ends of the filament. Silicon or Teflon is then injection-molded around the solder joint and the insulation around the conductors. Various components of the system are welded, soldered, or brazed, and after the assembly of components is completed, a thin aluminum coating or film (~5000 Å), for example, is over-coated on the tube to provide a path for the return current, as seen in FIG. 1. The thin aluminum has a high degree of x-ray transmission.

Where the components of the assembly are brazed, the following braze procedure may be as follows: The components are cleaned with acetone and a foil of incusil-15 ABA braze material, and are placed between the surfaces of the components to be brazed together. These components are then placed in a vacuum chamber and the chamber is evacuated with a vacuum pump to a pressure of $10^{-6}$ torr in about 30 minutes. The components are then heated under vacuum for 20 minutes to a temperature of 600° C. using a radiation heater. The components are held at this temperature for three minutes before being heated over a five-minute period to 750° C. The components are then held at 750° C. for five minutes, and then allowed to cool for more than one hour in the vacuum chamber, whereafter the brazed components are then removed from the vacuum chamber for use. Lower temperature brazing of some components has been achieved with the use of cusil ABA braze material.

The hot filament type cathode, embodiments illustrated in FIGS. 1–3, emits electrons which are then accelerated to the anode by the high voltage applied across the gap between the cathode and anode. In a tested prototype, a 1–2 volt, 0.5–1.0 amp current was used to heat a 25 micron diameter tungsten filament. The heating current produced thermionic electron emission. More efficient filament material, such as lanthium hexaboride, which requires lower power levels and lower temperatures could be used. The low voltage current can be precisely varied with a feedback circuit to control the high voltage current and provide greater reproducibility and stability than can be achieved with a field emission type or cold cathode. Also, current is independent of gap, and hot filaments tolerate worse vacuum conditions, wherein cold cathodes need 108 torr or better while hot cathodes only need $10^{-5}$ torr or better. The disadvantage is the need for a third conductor to supply the heating current for the filament. This can be overcome by using the center conductor to connect to the anode, as in the system of the above-referenced application. The external coaxial conductor can be used to provide the ground for the high voltage, as in the prior system, and also be used for the ground for the heating filament. The current source for the hot filament can be achieved using a pair of coaxial conductors, such as in triaxial cable, as shown in FIG. 1, or buried microsource sometimes used for sensors in medical catheters. The exterior thin aluminum coating on the vacuum housing must then be secured to the ground shield of the high voltage triaxial cable.

The general operation of the x-ray source, such as illustrated in the embodiments of FIGS. 1–3, is achieved by slowly increasing the voltage applied to the anode-cathode gap while the current is monitored between the filament and anode. This current is used to operate a feedback circuit controlling the filament current. If the filament to anode current drops, the filament current heating the filament produces more electrons. In this mode the voltage is raised to the level required to produce a given x-ray spectrum. The current regulation is then set to not exceed this current level. If the current starts to drop due to irreproducibility in the electrons from the hot filament, the power supply allows an increase in heating current in the filament, which increases the current to the anode back to the desired level. If the electron variations from the cathode increases the current, then the current regulation of the power supply reduces the heating current in the filament, which reduces the current. Since the current varies exponentially with the voltage, small variations in voltage which have minimal effect on the x-ray spectrum can be used to stabilize the hot filament electron production process.

Referring now to the drawings, FIG. 1 illustrates a preferred embodiment of a millimeter scale size x-ray source using a hot filament cathode in accordance with the present invention. As shown in FIG. 1, the embodiment comprises a vacuum housing or tube 10 constructed of a highly x-ray transparent material, such as sapphire, diamond, and PBN having an internal diameter of 1 mm and a wall thickness of 250 $\mu$ to 500 $\mu$; an end cap or plate 11 secured to an end 12 of vacuum housing 10 as by brazing, soldering, or welding; constructed of a conductive material such as copper or tungsten, and having a central opening 13 in which is mounted an anode, generally indicated at 14 and having a spherical end section 15 and a rod or stem section 16 which is mounted in opening 13 of end cap 11 as by brazing, soldering, or welding; an annular or donut shaped getter 17 extends around rod section 16 of anode 14 and is secured to end cap 11 as by bonding, brazing, soldering, etc., and may be composed of any getter material that does not require any power or processing after activation, such as SAES ST 707.

A hot filament cathode, generally indicated at 18, is mounted within vacuum housing or tube 10 in a selected spaced relation to anode 14 via a pair of standoff plates 19 and 20, which may be constructed of sapphire, Maycor, glass, or quartz. Standoff plate 19, which may have a thickness of 500 $\mu$ to 1 nm, is secured to tube 10 as by brazing, soldering, etc., and includes a pair of openings 21 and 22 in which a pair of feedthrus, 23 and 24, extend and are secured to standoff plate 19, as by brazing, soldering, etc. Feedthrus 23 and 24 may be constructed of a ceramic, such as alumina, or other electrically insulating materials that can withstand high voltages, such as Maycor, having opening or passageways 25 and 26 extending therethrough. Standoff plate 20 includes a pair of openings 27 and 28 into which ends of feedthrus 23 and 24 extend and are secured therein by brazing, soldering, etc., and thus standoff plate 20 is supported by standoff plate 19 via feedthrus 23 and 24. Cathode 18 includes a filament generally indicated at 29 and a focusing ring 30. The filament 29 includes a pair of leg sections 31 and 32 interconnected by a rounded or curved tip section 33, with leg sections 31 and 32 extending into openings or passageways 25 and 26 of feedthrus 23 and 24. Filament 29 may be constructed of tungsten or lanthium hexaboride having a diameter of 25 $\mu$ to 50 $\mu$, with round tip section having a curvature of 250 $\mu$ to 500 $\mu$, but such is not critical. By way of example, the rounded or curved tip section 33 of filament 29 of cathode 18 is positioned, for example, at a distance of 1 nm to 2 nm from the spherical section 15 of anode 14. The focusing ring 30 is secured to standoff 20. The focusing ring must extend about ½ inch beyond the filament to ensure focusing of all electrons onto the anode. The leg sections 31 and 32 are secured, as by brazing, soldering, etc., to a pair of conductors 34 and 35 of a triaxial cable generally indicated at 36. Triaxial cable 36 also includes insulation layers 37 and 38 around conductors 34 and 35 and a ground shield 39. As seen, the end of ground shield 39 and ends of insulation layers 37 and 38 are peeled back or removed, whereby conductors 34 and 35 extend into passageways 25 and 26, feedthrus 23 and 24 for connection to leg sections 31 and 32 of cathode filament 29. The area between standoff 19 and ground shield 39 of triaxial cable 36 is filled with a potting material 40, such as Teflon. A thin conductive coating 41, such as ~5000 Å of aluminum, for example, or other conductive material transparent to x-rays, is deposited on the outer surface of vacuum housing or tube 10, the peripheral edge of end cap 11, and onto ground shield 39 or triaxial cable 36 to provide an electrical return path. As pointed out above, the area indicated at 42 within tube or vacuum housing 10 in which anode 14 and cathode 18 are positioned is evacuated by an extended bake-out at high vacuum prior to end cap 11 being secured to tube 10, as by a vacuum brazing process. Focusing ring 30 includes an insulative coating 43.

FIG. 2 illustrates another embodiment of a hot filament cathode with a filament configured similar to the filament of FIG. 1, but with only one leg section constructed for connection to a high voltage power supply. As seen in FIG. 2, the cathode is located in a vacuum tube or housing 50, which may be constructed of PBN, sapphire, diamond, etc., and an anode 51 is mounted in an end of tube 50 by an end cap 52. A ceramic support member or standoff 53 having an opening 54 is secured in tube 50, and a feedthru 55 is mounted in opening 54. A getter 56 is secured to feedthru 55 and to a filament 57, which extends through feedthru 55 for connection to a power supply, not shown.

FIG. 3 illustrates an embodiment having cathodes similar to FIG. 1 and an anode similar to FIG. 2. As illustrated, the embodiment of FIG. 3 comprises a vacuum housing or tube 60 having an end cap 61 to which an anode 62 is secured. A standoff or support member 63 is mounted in tube 60 and includes a pair of openings 64 and 65 in which feedthrus 66 and 67 are secured, with feedthrus 66 and 67 having passageways 68 and 69 extending therethrough. A cathode, generally indicated at 70, having a filament 71 and a focusing ring 72 is located in vacuum tube 60, with filament 71 having leg sections 73 and 74 and a rounded tip section 75. Filament 71 is secured to feedthru 67 by an annular ring or member 76, with leg sections 73 and 74 extending into passageways 68 and 69 of feedthrus 66 and 67 for connection to a high voltage cable conductors 77 and 78, such as shown in FIG. 1. A getter 79 is secured to standoff 63 and focusing ring 72 is secured to getter 79.

Operation:

Electrical current to the filament is increased until filament is incandescent.

Free electrons are produced by thermionic emission.

The bias voltage between the filament and the anode is increased to the desired operating voltage (typically, 15 keV). Electrons are accelerated from the hot filament to the anode, where they produce x-rays via collisional impacts with the anode material. Regulation of the x-ray intensity is maintained by monitoring the filament of the anode current. If this current drops, then an electrical feedback circuit can be used to increase the electrical power in the filament increasing thermionic emission of electrons and restoring the desired current. If the current increases, the electrical power to the filament can be decreased, which decreases thermionic emission and reduces the current.

Focusing ring 72 acts as an electron lens. This partially focuses the electrons emitted from the filament onto the anode and prevents them from hitting the inner surfaces of the tube wall 60.

Focusing ring 72 will have its outer surfaces coated with an insulating material, such as aluminum oxide, sapphire, diamond, or other insulating material to improve its surface finish and provide additional insulation to prevent surface arcing within the tube.

The components of the FIGS. 2 and 3 embodiments may be constructed of materials and secured to associated components, as described above, with respect to FIG. 1.

It has thus been shown that the present invention provides a miniature x-ray source using a hot filament cathode which is capable of producing broad spectrum x-ray emission over a wide range of x-ray energies. The invention provides a compact x-ray source capable of handling high voltages over extremely small dimensions (~1 mm) high vacuum ($10^{-6}$ to $10^{-8}$ torr or better) in extremely small volumes (cubic mm), and a high voltage connection of extremely small size (~1 mm). The millimeter scale size x-ray source of this invention enables efficient production of x-rays with sufficient energy (~5–40 keV) force wide range of applications requiring the use of high voltages (~5–40 kV). Thus this invention provides a compact x-ray source, which has a wide range of applications in both the medical field and the material analysis field, since the source can be located in close proximity to the point of use.

While particular embodiments, materials, parameters, etc., have been illustrated and/or described to exemplify and teach the principles of the invention, such are not intended to be limiting. Modifications and changes may become apparent to those skilled in the art, and it is intended that the invention be limited only by the scope of the appended claims.

The invention claimed is:

1. In a miniature x-ray source having a vacuum housing containing at least one anode and a cathode, the improvement comprising:
   said cathode being of a hot filament type, and a getter operative connected to said cathode.

2. The improvement of claim 1, wherein said hot filament type cathode includes a filament having two leg sections interconnected by a curved end section, each of said leg sections being adapted to be connected to connectors of a high voltage cable.

3. The improvement of claim 1, wherein said hot filament type cathode includes a filament having one leg section and a curved end section, said one leg section being adapted to be connected to a conductor of a high voltage cable.

4. The improvement of claim 2, wherein said cathode additionally includes a focusing ring located around said hot filament.

5. The improvement of claim 2, wherein said curved end section of said filament is spaced from said anode of said x-ray source, and wherein said anode includes an end section of a configuration selected from the group consisting of curved and spherical.

6. The improvement of claim 5, wherein said anode is connected to an end cap of said vacuum housing.

7. The improvement of claim 6, additionally including a getter operative connected to said end cap.

8. The improvement of claim 2, wherein said getter is operatively secured to at least one leg section of said filament.

9. A millimeter scale size x-ray source comprising:
   an evacuated housing having at least a section of highly x-ray transparent material;
   an anode mounted in said housing;
   a hot filament type cathode located in said housing;
   at least one standoff mounted in said housing and having at least one opening therein;
   at least one feedthru mounted in said at least one opening in said standoff;
   said hot filament type cathode including a filament and a focusing ring;
   said filament having a pair of leg sections interconnected by a curved section;
   at least one of said leg sections of said filament extending into said at least one feedthru and adapted to be connected to a high voltage power source, and
   a getter located in said housing.

10. The x-ray source of claim 9, wherein said getter is mounted to said at least one standoff.

11. The x-ray source of claim 9, wherein said highly x-ray transparent material of said at least a section of said evacuated housing is composed of material selected from the group consisting of sapphire, diamond, and pyrolytic boron nitride.

12. The x-ray source of claim 9, wherein said anode is mounted in an end cap of said housing.

13. The x-ray source of claim 9, wherein said anode has an end section of a configuration selected from the group consisting of spherical and curved.

14. The x-ray source of claim 13, additionally including a getter secured to said end cap.

15. The x-ray source of claim 14, wherein said getter is of a donut shape.

16. The x-ray source of claim 9, wherein said at least one standoff is provided with a plurality of openings therein, and wherein a plurality of feedthrus are mounted in said openings of said at least one standoff.

17. The x-ray source of claim 16, wherein each of said pair of leg sections of said filament extend to one of said plurality of feedthrus.

18. The x-ray source of claim 17, wherein each of said pair of leg sections is connected to a conductor of a high voltage cable.

19. The x-ray source of claim 18, additionally including a thin layer of conductive, x-ray transparent material over said housing and in contact with high voltage cable.

20. The x-ray source of claim 9, wherein said getter is mounted to said at least one feedthru and to one of said leg sections of said filament.

21. The x-ray source of claim 9, additionally including a second standoff having at least one opening therein, and wherein said at least one feedthru extends into said at least one opening in said second standoff.

22. The x-ray source of claim 21, wherein said focusing rings of said cathode is secured to said second standoff.

* * * * *